(12) United States Patent
Elliott et al.

(10) Patent No.: US 6,451,368 B1
(45) Date of Patent: Sep. 17, 2002

(54) METHOD OF SELECTING NON-DIABETOGENIC MILK OR MILK PRODUCTS AND MILK OR MILK PRODUCTS SO SELECTED

(75) Inventors: Robert B Elliott, Auckland; Jeremy P Hill, Palmerston North, both of (NZ)

(73) Assignees: New Zealand Dairy Board, Wellington (NZ); A2 Corporation Limited, Dunedin (NZ)

(*) Notice: Subject to any disclaimer, the term of this patent is extended or adjusted under 35 U.S.C. 154(b) by 0 days.

(21) Appl. No.: 08/836,778

(22) PCT Filed: Nov. 3, 1995

(86) PCT No.: PCT/NZ95/00114
§ 371 (c)(1),
(2), (4) Date: Aug. 8, 1997

(87) PCT Pub. No.: WO96/14577
PCT Pub. Date: May 17, 1996

(30) Foreign Application Priority Data

Apr. 11, 1994 (NZ) ................................. 264862

(51) Int. Cl.$^7$ .............................. A23C 1/00; A23L 1/00; C12C 7/28; A61K 35/20
(52) U.S. Cl. ....................... 426/580; 426/531; 426/522; 426/613; 424/535
(58) Field of Search ....................... 119/14.02; 424/535; 514/866; 530/360, 361

(56) References Cited

FOREIGN PATENT DOCUMENTS

| EP | 0629350 A1 | 6/1994 |
|---|---|---|
| WO | WO 95/10537 | 10/1994 |
| ZA | 61/1804 | 5/1961 |
| ZA | 61/2068 | 8/1961 |
| ZA | 61/0600 | 2/1962 |

OTHER PUBLICATIONS

Beales et al., "Cow Milk Components and Diabetes Incidence in Rodent Models of Spontaneous Insulin Dependent Diabetest Mellitur", Abstract presented at the Second Worls Congress of Prevention of Diabetes and its Complications and the Fourth Immunology of Diabetes Society Congress in Fuigi, Italy from Nov. 10–15, 1999. (RB2).
Elliot et al., "Type I (insulin–dependent) diabetes mellitus and cow milk: casein variant consumption", Diabetologica 42: 292–296 (1999) (RBE3).
Padberg et al., Dtsch. Med. Wochenschr. 124: 1518021 (1999), Abstract (RBE4).
Olivares et al., Mol. Genet. Metab. 68:379–90 (1999) (RBE5).
Elliott et al., International Dairy Federation Newsletter, Brussels. special issue No. 9702:445–453 (1997) (RBE6).
Karges et al., Diabetes 46: 557–564 (1997), Abstract, RBE7.
Cavallo et al., Lancet 348:926–8 (1996), Abstract, RBE8.
Hermitte et al., Diabete Metab 21:261–8 (1995), Abstract, RBW9.
Scott and Marliss, Can. J, Physiol. Pharmacol. 69:311–9 (1991), Abstract, RBE10.
Coleman et al., Diabetes 39:432–6 (1990), Abstract, RBE11.
Elliott et al., Diabetologia 31:62–4 (1988), Abstract (RBE12).
Elliott and Martin, Diabetologia 26:297–299 (1984) (RBE13).
Petrilli et al. Biochem. Biophys. Res. Communic., 140:28–37, 1986.*
"Interaction of dietary protein and alpha–linolenic acid composition of liver microsomal . . . ", Ikeda and Sugan Sugano, Nutr. Metab (1993) vol. 37, pp. 101–109.
"A comparative study between the effect of feeding casein or beans on blood sugar, Serum Lipids . . . ", El–Harway et al., Egypt. J. Food Sci (1992) vol. 20(1), pp. 109–118.
"Milk proteins in the etiology of insulin–dependent diabetics Mellitus (IDDM)", Martin et al., Annals of Medicine (1991) vol. 23, pp. 447–452.
"Effect of dietary proteins on plasma lipid levels and lipoprotein lipid distribution in non–insulin . . . ", Chemical Abstracts, vol. 115(7), p. 670, col. 1, abstract No. 70271f, Domyak u Koka, 1991, (19(4), 223–6 Japan.
"The manufacture and industrial use of casein", Southward and Walker, New Zealand Journal of Dairy Science and Technology (1980), vol. 15, pp. 201–217.
"Occurrence of different beta–lactoglobulins in cow's milk", Aschaffenburg and Drewry, Nature (1955), pp. 176, 218–219.
"Association of genetic variants of casein and milk serum proteins with milk,fat, and protein production . . . ", Ng–K-wai–Hang et al., J Dairy Sci (1984), 67:835–840.
"Electrophoresis of cheese", Creamer (1991), Bulletin of the International Dairy Federation, Advanced Dairy Chemistry, vol. 1:Proteins, 261, International Dairy Federation, Brussels, Belgium.
"Genetic polymorphisms of the main bovine proteins", Grosclaude (1988) Production Animate, INRA, 1, 5–17.
"Biological properties of milk proteins", Fox and Flynn (1992), Advanced Dairy Chemistry, vol. 1:Proteins (Ed. Fox P F); pp. 255–284.

(List continued on next page.)

Primary Examiner—Deborah Crouch
Assistant Examiner—Thaian N. Ton
(74) Attorney, Agent, or Firm—Knobbe, Martens, Olson & Bear, LLP

(57) ABSTRACT

The invention is based on the discovery that certain variants of β-casein may induce Type-1 diabetes in susceptible individuals while other variants do not. The invention consists of the selection of non-diabetogenic milk producing cows and recovering and processing their milk and milk products. Another aspect of the invention is selectively breeding cows which produce the non-diabetogenic milk.

22 Claims, 3 Drawing Sheets

OTHER PUBLICATIONS

"The relationship between β–lactoglobulin phenotypes and milk composition in New Zealand dairy cattle", Hill (1993), J Dairy Sci, 76 281–286.

"Milk proteins: precursors of bioactive peptides", Meisel and Schlimme (1990) Trends in Food Science and Technology, X, 41–43.

"Biosynthesis of milk protein", Mepham et al., (1992) Advanced Dairy Chemistry vol. 1:Proteins (Ed. Fox P F) pp. 491–453.

"Specific binding sites on human phagocytic blood cells for Dly–Leu–Phe and Val–Glu–Pro–Ile–Pro–Tyr . . . ", Jaziri et al. (1992) Biochim, Biophys, Acta, 1160 251–261.

"Biologically active casein peptides implicated in immuno-modulation", Migliore–Samour et al., Journal of Dairy Research, 56, 357–362 (1989).

"Manufacture of casein, caseinates and co–precipitates", Muller (1986), Developments in Dairy Chemistry–1: Proteins (Ed. Fox P F), London, pp. 315–337.

"Genetic polymorphism of milk proteins", Ng–Kwai–Hang and Grosclaude (1992), Advanced Dairy Chemistry vol. 1:Proteins (Ed. Fox P F), London, pp. 405–455.

"Denaturation, aggregation and heat stability of milk protein during the manufacture of skim milk powder", Singh and Creamer (1991), Journal of Dairy Research, 58, 269–283.

"Chemistry of Caseins", Swaisgood (1992) Advanced Dairy Chemistry–vol. 1:Proteins (Ed Fox P F), London, pp. 63–110.

"Cow's milk, diabetes and infant feeding", Sheard (1993), Nutrition Reviews, 51 79–81.

"Perspective in diabetes: Early environmental events as a cause of IDDM: Evidence . . . ", Leslie and Elliott (1994), Diabetes 43, 843–850.

"Early introduction of dairy products associated with increased risk of IDDM in Finnish children", Virtanen et al. (1993) Diabetes 42 (Dec. 12), 1786–1970.

"Dietary protein: a trigger of insulin–dependent diabetes in the BB rat?", Elliott and Martin (1984), Diabetologia 26, 297–299.

"Epidemiology of diabetes in Polynesia and New Zealand", Elliott (1992), Pediatr. Adosesc. Endocrinol, Karger, Basal, 66–71.

"Casein peptide precipitates diabetes in the non–obese diabetic mouse and possibly humans", Elliott et al. (1992), Eds: Laron Z and Karp M Freund Publishing House Ltd.

Detection of multiple β–casein (CASB) alleles by amplification created restriction sites (ACRS), Lien et al. (1992), Animal Genetics 23, 333–338.

"Identification of a new genetic variant of bovine β–casein using reversed–phase high–performance liquid . . . ", Visser et al., Journal of Chromatography A, 711 (1995) 141–150.

* cited by examiner

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:BOVINE MILK
      PROTEIN

<400> SEQUENCE: 1

Pro Gly Pro Ile His Asn
1               5

<210> SEQ ID NO 2
<211> LENGTH: 209
<212> TYPE: PRT
<213> ORGANISM: Artificial Sequence
<220> FEATURE:
<223> OTHER INFORMATION: Description of Artificial Sequence:BOVINE MILK
      PROTEIN

<400> SEQUENCE: 2
```

-continued

```
Arg Glu Leu Glu Glu Leu Asn Val Pro Gly Glu Ile Val Glu Ser Leu
 1               5                   10                  15

Ser Ser Ser Glu Glu Ser Ile Thr Arg Ile Asp Lys Lys Ile Glu Lys
                20              25                  30

Phe Gln Ser Glu Glu Gln Gln Gln Thr Glu Asp Glu Leu Gln Asp Lys
            35              40                  45

Ile His Pro Phe Ala Gln Thr Gln Ser Leu Val Tyr Pro Phe Pro Gly
     50              55                  60

Pro Ile His Asn Ser Leu Pro Gln Asn Ile Pro Pro Leu Thr Gln Thr
 65              70                  75                      80

Pro Val Val Val Pro Pro Phe Leu Gln Pro Glu Val Met Gly Val Ser
                 85              90                  95

Lys Val Lys Glu Ala Met Ala Pro Lys His Lys Glu Met Pro Phe Pro
            100             105                 110

Lys Tyr Pro Val Gln Pro Phe Thr Glu Ser Gln Ser Leu Thr Leu Thr
            115             120                 125

Asp Val Glu Asn Leu His Leu Pro Pro Leu Leu Leu Gln Ser Trp Met
        130             135                 140

His Gln Pro His Gln Pro Leu Pro Pro Thr Val Met Phe Pro Pro Gln
145             150                 155                     160

Ser Val Leu Ser Leu Ser Gln Ser Lys Val Leu Pro Val Pro Glu Lys
                165             170                 175

Ala Val Pro Tyr Pro Gln Arg Asp Met Pro Ile Gln Ala Phe Leu Leu
            180             185                 190

Tyr Gln Gln Pro Val Leu Gly Pro Val Arg Gly Pro Phe Pro Ile Ile
        195             200                 205

Val
```

METHOD OF SELECTING NON-DIABETOGENIC MILK OR MILK PRODUCTS AND MILK OR MILK PRODUCTS SO SELECTED

TECHNICAL FIELD

This invention relates to a method for avoiding the triggering of Type 1 diabetes in humans by the ingestion of milk or milk products. More particularly, the method relates to the selection of milk which does not contain a diabetogenic factor by selecting cows producing milk which contains any variant of β-casein which does not stimulate diabetogenic activity in humans (a non-diabetogenic variant) to the exclusion of any variant of β-casein which does stimulate diabetogenic activity in humans (a diabetogenic variant).

BACKGROUND ART

Type 1 diabetes occurs in individuals who are genetically susceptible. However, even in identical twins, diabetes may occur in one and not in the other. The present invention relies upon the discovery of an environmental trigger for Type 1 diabetes which operates very early in life.

The evidence that this environmental trigger is to be found in cows milk is based on epidemiological (Leslie et al, 1994), ecological (Virtanen et al, 1993) and animal experimental evidence (Elliott & Martin, 1984 and Elliott 1992). The diabetogenic factor of the milk appears to be in the casein fraction (Elliott et al, 1992), at least in the non-obese diabetic (NOD) mouse. Whey protein does not appear to, contain any diabetogenic component (Elliott et al, 1992). It has been suggested that bovine serum albumin (BSA), a protein found in the whey fraction of cows milk is the diabetogenic component of cows milk (Sheard, 1993). However, a review of the evidence supporting this theory does not indicate that BSA was ever tested for diabetogenic activity in the absence of β-casein.

International PCT Application WO95/10537 discloses a method of producing denatured bovine serum albumin milk products. It is stated that the consumption of denatured BSA milk products tends to reduce the likelihood of a person acquiring type 1 diabetes. However, there is no evidence presented of any trials where either human or animal subjects were fed milk or milk products with denatured BSA. It relies upon the theory mentioned above that BSA is the diabetogenic component of cows milk (Sheard, 1993). In European Patent Application 629,350 there is described a method of hydrolysing cows milk protein to produce a hydrolysates substantially free of allergenic proteins. The hydrolysate also is suggested to be useful in the prophylaxis and treatment of type 1 diabetes melitis in children susceptible to such disease. In the description on page 6 of that specification it is suggested that BSA may be a trigger to the immune system. However, there are no examples in the patent specification and no reference to any papers showing any direct evidence of this suggestion.

In South African patent specifications 61/1804 laid open on Jun. 28, 1961, 61/2068 laid open on Sep. 20, 1961 and 62/600 laid open on Jul. 4, 1962 there are described compositions alleged to be cures for diabetes. There are no examples of any trials in support of these assertions. The compositions consist of casein as a base and fruit and leaves of South Africa plants. It is inferable from the description that the active ingredient is the plant material and there is no mention that casein has any role in causing or curing diabetes.

We have now tested the A1 and A2 variants of β-casein and a whey protein on NOD mice and found that the A1 variant does have diabetogenic activity while the A2 variant and whey protein do not show diabetogenic activity.

It is an object of one aspect of the invention to use this finding to go some way to selecting milk and milk products which do not contain a diabetogenic factor in such milk or milk product or at least to offer the public a useful choice.

It is an object of another aspect of this invention to go some way towards selectively breeding cows and bulls whose offspring produce milk which is not diabetogenic or which at least offers the public a useful choice.

DISCLOSURE OF THE INVENTION

Accordingly, the invention may be said broadly to consist in a method of selecting milk for feeding to diabetes susceptible individuals which comprises testing milk from identified cows for the presence of variants of β-casein and selecting those cows whose milk contains any non-diabetogenic variant and does not contain any diabetogenic variant, and milking separately the non-diabetogenic variant milk producing cows and recovering and maintaining their milk separately from milk from any other source.

Preferably said non-diabetogenic variant is the A2 variant of β-casein.

Alternatively said non-diabetogenic variant is the A3, D or E variant of β-casein.

Preferably said diabetogenic variant is the A1 variant of β-casein.

Alternatively, said diabetogenic variant is any one of the B, C and F variants.

Preferably, said recovered milk is tested for the presence of any diabetogenic variant and discarded if any is found.

Alternatively, said method of testing comprises the use of mass spectrometry.

In one embodiment said mass spectrometry comprises electro spray ionisation mass spectrometry.

Alternatively, said mass spectrometry comprises fast-atomic bombardment mass spectrometry.

Preferably, said method of testing comprises polyacrylamide gel electrophoresis using an acid urea gel.

Preferably, said process includes the additional step of processing said milk into milk products.

There are a large number of processes known to those skilled in the art for converting milk into milk products. These range from separating cream from whole milk to produce skim milk through to the use of microfiltration and ultrafiltration to produce a wide range of products such as those described in international application PCT/NZ95/00086, the specification, claims and drawings of which are incorporated herewith by reference.

One particular product of interest from the aforementioned international application is milk protein concentrate. This may be prepared by other processes such as that described in IDF Special Issue No. 9201, (1991), Chapter 5 entitled "Milk Protein Concentrate", A. Novak.

Another milk product according to the invention is casein derived from non-diabetogenic milk by any well known casein producing process such as described in Southward et al, 1980.

The invention may be said broadly to consist in milk selected according to the process herein above defined.

The invention may also be said broadly to consist in a non-diabetogenic milk product prepared by any one of the processes described herein above.

The invention may also be said broadly to consist in a method for reducing the risk of contracting type 1 diabetes in a susceptible individual which comprises restricting the milk or milk product intake of that individual to milk containing only a non-diabetic variant of beta casein.

Preferably, said susceptible individual is an infant or young child.

The invention may also be said broadly to consist in a method of selecting milk for feeding to a Type-1 diabetes susceptible individual which comprises testing milk from identified cows for the presence of the hexapeptide Pro-Gly-Pro-Ile-His-Asn (SEQ ID NO: 1), or a protein fragment containing the hexapeptide Pro-Gly-Pro-Ile-His-Asn (SEQ ID NO: 1) and selecting those cows whose milk does not contain said hexapeptide or said protein fragment containing said hexapeptide, and milking separately the cows whose milk does not contain the said hexapeptide or said protein fragment containing said hexapeptide and maintaining their milks separately from milk from any other source.

Preferably, said separated milk is also tested for the presence of said hexapeptide or said protein fragment containing said hexapeptide and any milk which does contain said hexapeptide or said protein containing hexapeptide is discarded.

Preferably, the method of testing for said hexapeptide is by using chromatographic purification of said hexapeptide followed by amino acid sequencing.

Preferably, said process includes the additional step of processing said milk into milk products.

The invention may be said broadly to consist in milk selected according to the process herein above defined.

The invention may also be said broadly to consist in a non-diabetogenic milk product prepared by any one of the processes described herein above.

Preferably, said susceptible individual is an infant or young child.

In another embodiment the invention may be said broadly to consist in a method for selecting breeding cows which produce daughters whose milk is not diabetogenic to susceptible children which comprises determining the genotype of said cows and selecting those whose daughters produce milk which does not contain the diabetogenic factor present in β-casein.

Alternatively, the invention may be said broadly to consist in a process for selectively breeding bulls which produce daughters whose milk does not contain the diabetogenic factor present in β-casein which comprises determining the genotype of said bulls and selecting those which daughters which produce milk which does not contain the diabetogenic factor present in β-casein.

Preferably, the phenotyping of daughters to determine the genotype of said bull is done by testing the milk of said daughters for absence of diabetogenic variants of β-casein and the presence of non-diabetogenic variants of β-casein.

Alternatively, said cows or bulls are genotyped directly by using appropriate probes and polymerase chain reaction technology.

In another embodiment the invention may be said broadly to consist in cows selected in accordance with the immediately preceding method.

In a still further embodiment the invention may be said broadly to consist in bulls selected in accordance with the above defined method.

In a still further embodiment the invention may be said broadly to consist in semen of bulls selected in accordance with the above defined method.

In an alternative to any of the above processes or products the milk or milk product is goat's milk or milk product, sheep's milk or milk product, buffalo's milk or milk product, or milk or milk product from any other mammal which is fit for human consumption.

MODES OF CARRYING OUT THE INVENTION

Milk Protein Polymorphism

Figure 1:
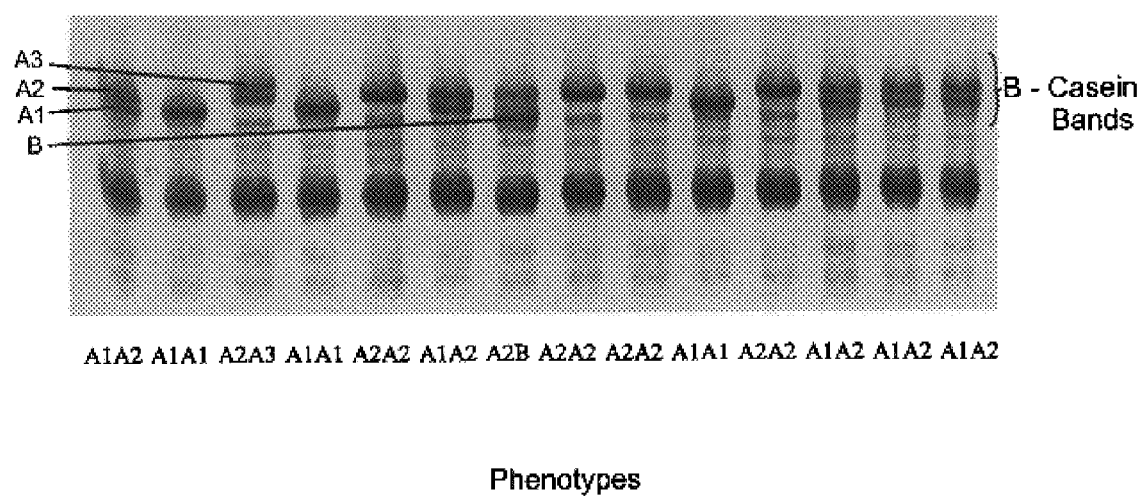
FIG. 1 is a photograph of PAGE bands of β-casein variants.

Following the initial discovery by Aschaffenburg and Drewry (1955) that the major whey protein in milk, β-lactoglobulin is found in a number of variant forms, all major milk proteins ($\alpha_{S1}$-casein, $\alpha_{S2}$-casein, β-casein, κ-casein and α-lactalbumin) are now also known to exist as a number of variant protein species, due to genetic polymorphism at the gene loci coding for these proteins (Grosclaude, 1988, Ng-Kwai-Hang and Grosclaude, 1992). The primary sequences of the casein proteins and a comprehensive list of the amino acid sequence changes that give rise to the variant forms of these proteins is given by Swaisgood (1992), Ng-Kwai-Hang and Grosclaude (1992) and Visser et al (1995). The protein β-casein has eight variant forms:

A1 A2 A3 B C D E F

As highlighted by Ng-Kwai-Hang and Grosclaude (1992) the A2 variant is considered to be the original variant type of the Genus Bos.

Because the milk protein genes are expressed codominantly (Mepham et al, 1992), individual cows produce milk containing either a single variant form of β-casein (A1A1, A2A2, A3A3 phenotype cows etc) or a mixture of two variant forms of β-casein (A1A2, A1A3, A2A3 phenotype cows etc). The frequency of β-casein phenotypes in a sample population of New Zealand dairy cows expressed as percentages is set out in Table 1.

TABLE 1

| | Phenotype | | | | | | | |
|---|---|---|---|---|---|---|---|---|
| Breed | A1A1 | A1A2 | A1A3 | A1B | A2A2 | A2A3 | A2B | BB |
| Friesian | 21 | 43 | 0.1 | 5 | 24 | 0.16 | 5.6 | 0.4 |
| Jersey | 0 | 9 | 0 | 5 | 46 | 0 | 34 | 6 |

The predominant β-casein variant from the Indian cow (*Bos indicus*) is identical in its amino acid sequence to the A2 variant of the common dairy cow (*Bos taurus*). The Maasai people of Central Africa drink large quantities of cows milk from *Bos indicus* from very early life, but do not develop diabetes, whereas Finnish people who drink similarly large quantities of milk from mixed *Bos taurus* herds have a very high diabetes incidence.

Although the examples of this specification relate to milk from cows there is no reason to doubt that the processes and products described are equally applicable to milk from any mammalian source which is fit for human consumption.

EXAMPLE 1

Finnish and Samoan Diets Fed to NOD Mice

Based on these observations we have assessed the effect of human infant diets given to 1 year old normal Finnish children (who have a subsequent risk rate of diabetes of 40/100,000/yr in the following 15 years), and similar diets collected from Samoan children (in which the subsequent expected diabetes incidence is <1/100,000/yr) on the diabetes prone NOD mouse.

Diets from Finnish and W. Samoan children were collected from 10 children from each location. The children were 10–14 months old. The families were cooperative middle-class and the collections were supervised by a trained dietitian, who also asked the parents to provide a record of the types and quantities of food given.

As each portion of food or drink was given to the infant a similar quantity was placed in a container. This was kept frozen until a total of 10 days equivalent food was collected. Thereafter the food was freeze dried and then shipped to New Zealand. The food was sterilized by gamma radiation before being given to the mice.

Children in these two groups consumed<100 ml and >500 ml of cows milk per day respectively in Samoa and Finland.

The diets were then fed to groups of NOD mice from weaning either as the sole dietary or as a 10% w/w addition to a soy based infant formula Prosobee™ previously shown not to cause diabetes in this strain of mouse. The diabetes incidence in the succeeding 250 days was then assessed. The results are shown in Table 2. The Finnish diet is more (about threefold) diabetogenic than the Samoan diet and this corresponds approximately to the relative proportion of cows milk in the two diets.

"versus". In this instance the p value of 0.112 means that this result could have arisen by chance 11.2 times out of 100. IF means infant formula.

EXAMPLE 2

NOD Mice Fed Hydrolysed Casein and Casein

Similar groups of mice were fed a diet whose sole nitrogen source was hydrolysed casein or casein itself. Only the casein fed mice developed diabetes (Table 3).

TABLE 3

Effect of casein hydrolysed infant formula (Pregestimil ™) and similar intact casein infant formula (Portagen ™) on diabetes incidence in NOD mice fed these diets from weaning

| Type | No. of Animals | No. of Animals Developing Diabetes | Percentage | "P" Value (Fisher Exact Test) |
|---|---|---|---|---|
| Hydrolysed casein | 49 | 1 | 2 | .001* |
| Intact casein | 29 | 8 | 28 | |

EXAMPLE 3

NOD Mice Fed $A_1$ and $A_2$ Variants of Cow β-casein and Whey Proteins

Similar groups of mice were fed a diet of the soy infant formula Prosobee™ and 10% W/W of:

a) β-casein A1 variant,
b) β-casein A2 variant,
c) whey,
d) Bos indicus casein, or
e) a 50/50 mixture of β-casein A1 variant/A2 variant.

TABLE 2

Effect of duplicate infant diets from Finland and Western Samoa on diabetes incidence in NOD mice fed these diets from weaning.

| | | Diet | No. of Animals | No. of Animals Developing Diabetes by 250 days | % | "p" Value (Fisher Exact Test) |
|---|---|---|---|---|---|---|
| 1 | a) | Western Samoan diet | 24 | 14 | 58 | avb |
| | b) | Finnish diet | 20 | 16 | 80 | 0.112 |
| 2 | a) | 10% Western Samoan diet in Prosobee ™ IF | 43 | 4 | 9 | avb .007* |
| | b) | 10% Finnish diet in Prosobee ™ IF | 39 | 13 | 33 | |
| 3 | | Prosobee ™ IF alone | 33 | 0 | 0 | Prosobee ™ IF v2a.113 Prosobee ™ IF v2b.00Q* |

The "p" value is the statistical estimate of the strength of the observation that there is a difference between the two groups. In general a "p" value of less than 0.05 is accepted as highly significant, and has been asterisked. The other symbols in each box refer to the comparison being made e.g. in the first box "a" refers to 1a i.e. the proportion 14/24 and the symbol "b" to the proportion 16/20 the "v" is merely The subsequent diabetes incidence in the groups is shown in Table 4. The β-casein A1 variant precipitated diabetes in 9 of 20 cases, the A2 variants in no cases and the A1/A2 mixture in 4 of 20 cases. The result mid-way between the A1 and A1 alone results is consistent with there being no interaction between A1 and A2. Only seven percent of the whey protein fed mice developed diabetes.

TABLE 4

Effect of bovine β-casein A1 and A2 variants and whey proteins on diabetes incidence in NOD mice fed these proteins as 10% additions to Prosobee ™ infant formula from weaning

| | | Number of Animals | Number of Animals Developing Diabetes by 250 days | Percentage | "P" Value (Fisher Exact Test) |
|---|---|---|---|---|---|
| a) | 10% β-casein A1 variant | 20 | 9 | 45 | avb .001* avc .003* |
| b) | 10% β-casein A2 variant | 18 | 0 | 0 | bvc N.S. |
| c) | 10% whey | 29 | 2 | 7 | |
| d) | 10% Bos indicus casein* | 20 | 0 | 0 | bvd N.S |
| e) | 10% β-casein A1/A2 variants (equal mixture) | 20 | 4 | 20 | |

*Known to contain only the A2 variant (see Example 7)

From the animal experiments in Examples 1 to 3 it can be concluded that mixed dairy casein is diabetogenic in the NOD mouse and that this property resides in the β-casein A1 variant.

EXAMPLE 4

Acid Urea Method for Typing Milk for β-casein Variant

The polyacrylamide gel electrophoresis (PAGE) was carried out on a Biorad Mini Protean II system (supplied by Biorad Laboratories, Hercules, Calif., USA). The method separates qualitatively variants of β-casein by net charge and molecular weight.

All the reagents are analytical grade unless otherwise stated.

28.5 ml of glacial acetic acid was diluted to 500 ml with deionised water (Milli-Q water) to make the buffer. 500 ml of buffer was used per run.

Acid Urea Stacking Gel Solution

The acid urea stacking gel solution was made up by weighing up the following reagents and dissolving them in Milli-Q water to approximately 80 ml. The pH was adjusted to 4.1 with acetic acid and made up to 100 ml in a measuring cylinder.

36.04 g urea
6.0 g acrylamide/bis premix (5% C) Serva
0.113 g ammonium acetate
0.178 g thiourea
1.48 ml glacial acetic acid Acid Urea Resolving Gel Solution The following reagents were dissolved in Milli-Q water to approximately 130 ml, the pH adjusted to 3.86 with acetic acid and made up to 150 ml in a measuring cylinder.

9.75 g Acrylamide/bis premix (5% C) Serva Research Grade
40.36 g urea
9.48 ml glacial acetic acid
0.72 g ammonium acetate
0.26 g thiourea Acid Urea Sample Buffer An acid urea sample buffer was made up by weighing out the following reagents and dissolving them in approximately 350 ml of Milli-Q water. The pH was adjusted to 4.16 with acetic acid and the volume made up to 400 ml.

163.18 g urea
6.69 ml glacial acetic acid
0.451 g ammonium acetate

A solution of Bromophenol Blue (0.4 w/v) was made up by dissolving 1.6 gms of bromophenol blue with 6.8 ml of NaOH (0.1 m). This was then made up to 400 ml with Milli-Q water.

A distaining solution was made up by mixing 8 liters of Milli-Q water, 1000 ml of glacial acetic acid and 1000 ml of isopropanol.

A Coomassie blue R stain was made up by dissolving 1.00 gms of brilliant blue R in 500 ml isopropanol, adding 200 ml of glacial acetic acid and making up to 2 liters with Milli-Q water. The solution was covered with a gas tight cling wrap and stirred overnight. The stain was filtered using a Buchner funnel and Whatman number 1 filter paper.

The resolving gel solution was placed between the glass plates of an electrophoresis apparatus. The stacking gel was also placed between the glass plates and allowed to polymerise according to known techniques.

The β-casein variant samples were added in 25 μl aliquots to 750 μl of sample buffer. 10 μl of 2-mercaptoethanol was added and the samples allowed to stand at least one hour at room temperature or 4° C. overnight. The samples were run in sample slots. The samples were injected by syringe.

The power pack of the apparatus was set to deliver:

| | | |
|---|---|---|
| Program | = | T/V-H |
| Current | = | 70 mA |
| Field strength | = | 210 V |
| Watt power | = | 6.5 |
| Time | = | 1 hour for 2 gels |

After the running time of one hour the power pack was turned off and the power cables disconnected. The gel was pealed off the plate of the apparatus into the container of stain (approximately one hour). After distaining in distaining solution (less than one hour) the gel container was put onto a light box and a photograph taken to identify the bands.

The bands as photographed are shown in FIG. 1. The samples in the lanes are identified. The banding pattern for β-casein variant proteins on an acid urea PAGE gel is, starting from the top, A3 variant, A2 variant, A1 variant and B variant

EXAMPLE 5

Reverse Phase HPLC and Mass Spectromatic Analysis Method of Typing Milk for β-Casein Variant β-casein variants in milk may be typed using the method of Visser et al (1995). In Visser's paper the F variant was identified by using reversed phase HPLC followed by electrospray ionisation and fast atom bombardment to determine molecular weights and characterize the amino acid substitutions in the protein. The other variants can be determined using the same techniques.

EXAMPLE 6

Direct Genotyping of Cows or Bulls

DNA extracted from frozen bull semen was directly sequenced by polymerise chain reaction (PCR) to detect the sequences for bovine β-casein variants according to the method of Lien et al (1992).

Semen containing the non-diabetogenic alleles detected can be used in a breeding programme.

EXAMPLE 7

Separation of β-casein A1 and A2 Variants

1. Phenotype Identification

Cows (*Bos taurus*) homozygous for the β-casein variant A1 and A2 genes (β-casein A1A1 and A2A2 phenotype cows) were identified by polyacrylamide gel electrophoresis (PAGE) of milk samples from individual cows using the acid urea gel system as described in Example 4.

Samples of New Zealand casein (Alacid 710™) and casein prepared from the milk supplied from a herd of Australian Bos indicus cows were also subjected to PAGE as described above in Example 4. Alacid 710™ casein is manufactured from bulk New Zealand milk which in turn is produced from many thousands of cows of different β-casein phenotypes.

The relative amounts of the different genetic variants of β-casein in Alacid 710™ casein were determined by computing densitometry in a method described by Hill (1993) and Singh and Creamer (1991). The results are tabulated in Table 5.

TABLE 5

| β-casein Variant | % Amount in Alacid 710 | Range (N = 9) |
| --- | --- | --- |
| A1 | 40.0 | 38.4–41.4 |
| A2 | 51.5 | 48.1–53.3 |
| B | 7.5 | 6.5–8.5 |
| A3 | 1.0 | 0.2–1.7 |

The Australian Bos indicus casein was found to contain only the β-casein A2 variant.

2. Milk Production, Segregation and Collection

From a total of 3183 cows located on 25 large farms in the Manawatu and Waikato regions of New Zealand, approximately 400 cows were selected and placed on a single farm as a mixed herd such that the β-casein A1A1 and A2A2 phenotype cows in this herd were subjected to identical farm management and feeding practices. Milk supplied from either β-casein A1A1 or A2A2 phenotype cows was segregated by the use of dual milk lines situated in the farm milking parlour and collected in separate refrigerated vats essentially as described by Hill (1993). The bulked β-casein A1A1 and A2A2 phenotype milks were then pumped into separate compartments of milk tanker before tankering to the New Zealand Dairy Research Institute Pilot Plant.

3. Casein Manufacture

Lactic casein was manufactured in the New Zealand Dairy Research Institute Pilot Plant from the β-casein A1A1 and A2A2 phenotype bulk milks using methods essentially identical to those used in a standard New Zealand commercial lactic casein manufacturing dairy factory (see Muller, 1986). These caseins together with other constituents were then used in the feeding trials as described in Examples 2 and 3.

EXAMPLE 8

Immunostimulating Peptides from β-casein

Figure 2:
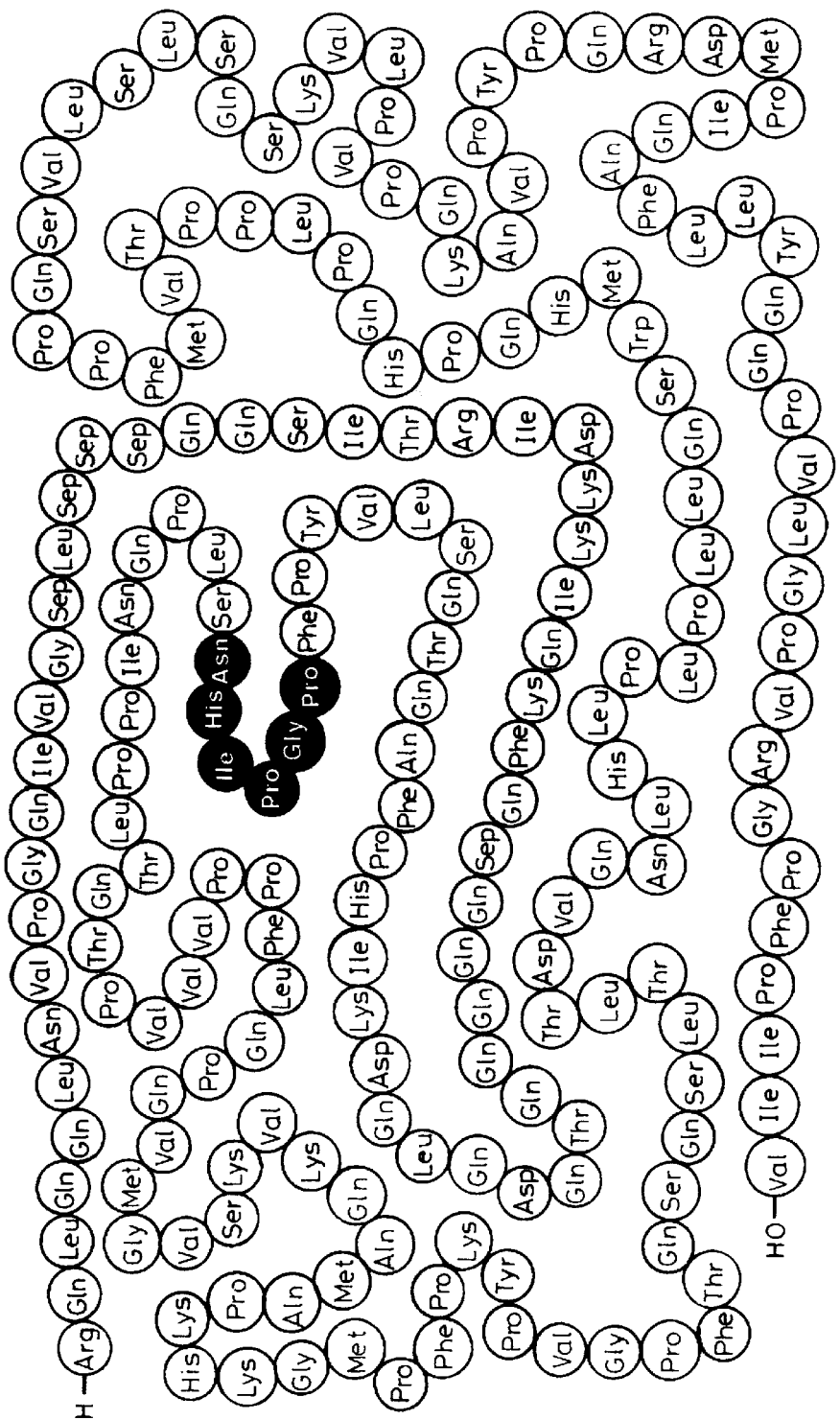
FIG. 2 is a protein sequence representation of the bovine β-casein A1 variant (SEQ ID No: 2).

Partially hydrolysed mixed caseins containing a variety of peptides are also diabetogenic, whether given in soy formula in the diet or by injection into mice fed on the soy formula. This suggests that the intact casein molecules may not be necessary for the diabetogenic action. Among the peptides resistant to hydrolysis is the hexapeptide Pro-Gly-Pro-Ile-His-Asn (SEQ ID NO: 1) shown in FIG. 2.

Peptides of β-casein have been found to stimulate the human immune systems (Meisel and Schlimme, 1990; Fox and Flynn, 1992). M'Hamiel Jzairi et al (1992) have shown that there is a specific binding site on the human macrophage for the immunostimulating peptide Val-54 to Tyr-59 from human β-casein. Although the hexapeptide Pro-63 to Asn-68 from bovine β-casein (highlighted in the complete β-casein A1 variant amino acid sequence shown in FIG. 2) has been found to stimulate the phagocytic activity of murine macrophages (Migliore-Samour et al, 1989) the binding of this peptide to human macrophages has until now not been demonstrated.

Using the method described by M'Hamiel Jaziri et al (1992) the human macrophage binding of the bovine peptides Pro-63 to Asn-68 (from the β-casein A1 and A2 variant sequences) were studied and compared with the binding of the peptide Val-54 Tyr-59 from human β-peptide to each of a normal human macrophage and a prediabetic human macrophage. The results are set out below in Table 6. They show that both bovine A1 and A2 and human hexapeptides bind specifically both to normal human macrophages and to prediabetic macrophages, implying some immune function.

With the small numbers involved (three subjects in each group) the "prediabetic" macrophages bind the peptides with an avidity order of A1>A2>human, whereas the normal macrophages bind A1=A2=human. A2 is bound to the same extent by normal and prediabetic macrophages. This means that the prediabetic macrophages are more likely than normals to present the A1 peptide to the immune system, which may account for the higher levels of antibody to the A1 casein variant found in newly diagnosed diabetics.

TABLE 6

Binding of tritiated hexapeptides to PB monocyte/Macrophages
(+ Glucose, NaN3, Captopril, Benzylsuccinate, Elastatinal)

| Peptide | CPM | Ratio */** |
| --- | --- | --- |
| NORMAL PBM (N = 3) | | |
| Human | 2750* | 1.2 |
| Bovine A1 | 2220** | |
| A2 | 2900 | |
| PREDIABETIC PBM (N = 3) | | |
| Human | 1400* | 0.31 |
| Bovine A1 | 4500** | |
| A2 | 2750 | |

The β-casein A3, D and E variants each contain an identical hexapeptide sequence between Pro-63 and Asn-68 to that found in the β-casein A2 variant (proline at position 67), however the β-casein A1, B, C and F variants proline-67 is substituted by a histidine residue.

Figure 3:
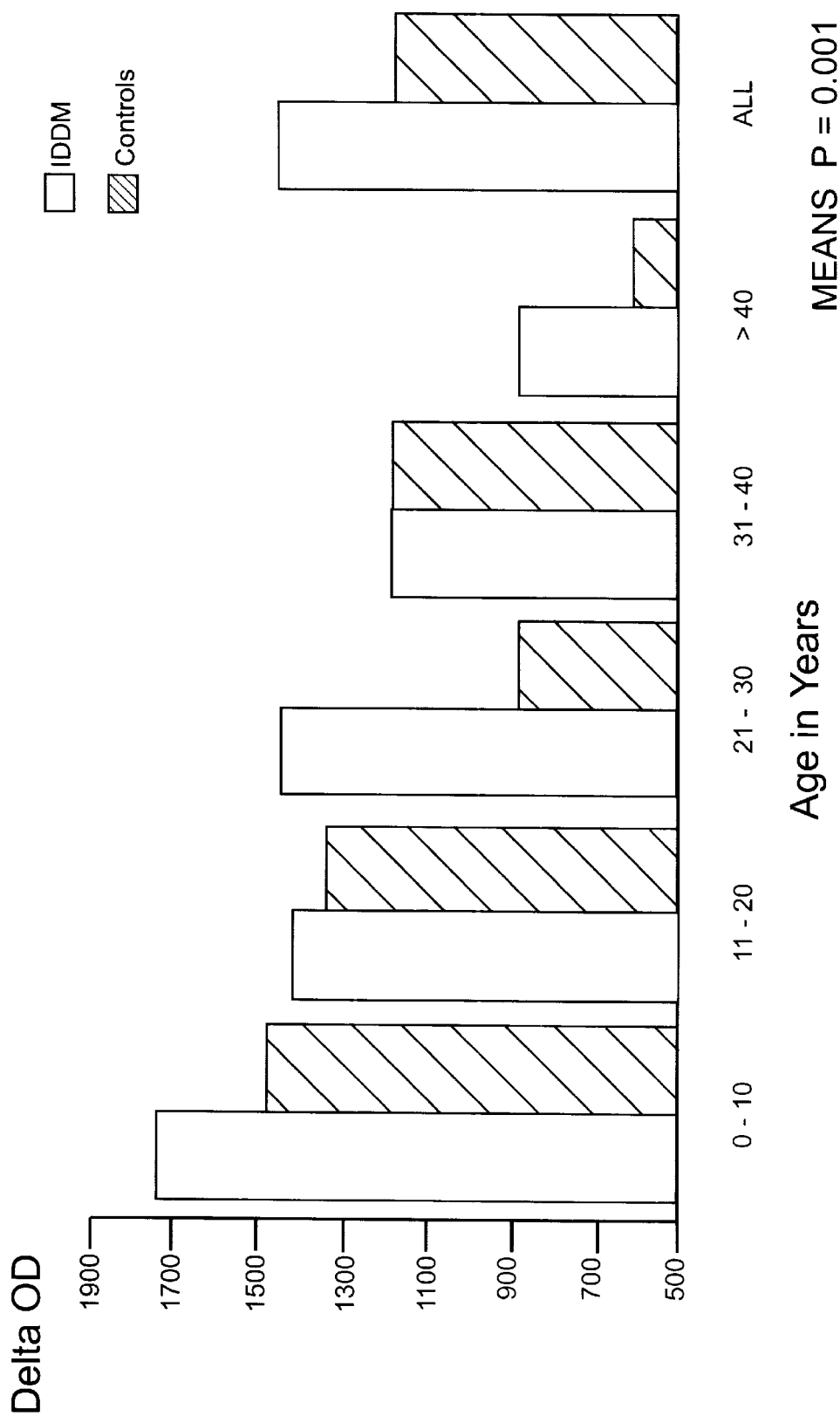
FIG. 3 is a bar graph of differences in antibody levels to mixed β-casein variants in human patients of different ages with recently diagnosed diabetes against controls.

Antibodies to mixed caseins are found at higher levels in newly diagnosed diabetics (IDDM) than in normal controls (FIG. 3) and, this difference appears to reside in the higher levels of antibodies directed against A1 rather than A2 caseins in the diabetics. Testing of the antibodies was done by Enzyme Immuno-Assay. In this the caseins are bound to the wall of a plastic container and the serum containing the antibodies then brought into contact with this bound casein. After incubation the serum is decanted and any antibody present will have become bound to the casein. This bound antibody is then measured by a colour reaction.

From the above it can be concluded that cows milk β-casein A1 variant is diabetogenic in the NOD mouse identical with A2 variant, (the Maasai), it is likely that β-casein A1 variant is the principal moiety in cows milk which is diabetogenic in humans.

EXAMPLE 9

The Measurement of Anti-Casein Antibodies in Newly Diagnosed Diabetics and Age Matched Normals Antibodies were measured by an ELISA technique utilising immunoglobulin G subclass measurement to develop the class specific antibody levels.

TABLE 7

Levels of Antibodies to Purified A1 and AZ Beta Casein Classified by Subtype of IgG

| | | Diabetics are at onset (children age 1–12 yr) Diabetic | | | | normals (age matched) Normal | | | |
|---|---|---|---|---|---|---|---|---|---|
| IgG class (OD) | | 1 | 2 | 3 | 4 | 1 | 2 | 3 | 4 |
| #1 | A1 | .086 | 0 | 0 | 0 | 0 | 0 | 0 | 0 |
| | A2 | .072 | 0 | 0 | 0 | 0 | 0 | 0 | 0 |
| #2 | A1 | .029 | 0 | .038 | 0 | 0 | 0 | 0 | 0 |
| | A2 | 0 | 0 | .022 | 0 | 0 | 0 | 0 | 0 |
| #3 | A1 | .106 | .048 | .138 | .610 | 0 | 0 | 0 | 0 |
| | A2 | .045 | .056 | .104 | .529 | 0 | 0 | 0 | 0 |
| #4 | A1 | 0 | 0 | 0 | 0 | 0 | 0 | 0 | 0 |
| | A2 | 0 | 0 | 0 | 0 | 0 | 0 | 0 | 0 |
| #5 | A1 | .021 | 0 | .237 | 0 | 0 | 0 | 0 | 0 |
| | A2 | 0 | 0 | .250 | 0 | 0 | 0 | 0 | 0 |
| #6 | A1 | .098 | .042 | .025 | 1.374 | 0 | 0 | 0 | 0 |
| | A2 | .052 | .022 | 0 | 1.110 | 0 | 0 | 0 | 0 |
| #7 | A1 | .075 | 0 | 0 | .165 | 0 | 0 | 0 | .083 |
| | A2 | .057 | 0 | 0 | .099 | 0 | 0 | 0 | .052 |
| #8 | A1 | .128 | 0 | .028 | .219 | 0 | 0 | 0 | 0 |
| | A2 | .068 | 0 | 0 | .066 | 0 | 0 | 0 | 0 |
| #9 | A1 | .210 | .049 | .195 | .397 | 0 | 0 | 0 | .03 |
| | A2 | .197 | .043 | .155 | .397 | 0 | 0 | 0 | 0 |
| #10 | A1 | .669 | 0 | .286 | .539 | 0 | 0 | 0 | 0 |
| | A2 | .606 | 0 | .272 | .525 | 0 | 0 | 0 | 0 |
| #11 | A1 | 0 | 0 | .171 | .162 | .249 | .041 | .213 | .052 |
| | A2 | 0 | 0 | .144 | .171 | .272 | .043 | .174 | .044 |
| #12 | A1 | .045 | 0 | .061 | .039 | .372 | 0 | .385 | .233 |
| | A2 | 0 | 0 | .046 | 0 | .256 | 0 | .362 | .031 |
| #13 | A1 | .023 | 0 | .066 | 0 | .051 | 0 | .026 | 0 |
| | A2 | 0 | 0 | .046 | 0 | .04 | 0 | .026 | 0 |
| #14 | A1 | 0 | 0 | 0 | 0 | 0 | 0 | .056 | .021 |
| | A2 | 0 | 0 | 0 | 0 | 0 | 0 | .051 | 0 |
| #15 | A1 | .042 | 0 | .124 | .035 | .083 | 0 | .242 | .129 |
| | A2 | .054 | 0 | .114 | .036 | .071 | 0 | .246 | .129 |
| #16 | A1 | .154 | 0 | .234 | .061 | 0 | 0 | .092 | 0 |
| | A2 | .106 | 0 | .234 | .051 | 0 | 0 | .103 | 0 |
| #17 | A1 | .132 | .069 | .285 | .139 | .073 | 0 | .147 | .079 |
| | A2 | .097 | .052 | .254 | .153 | .063 | 0 | .109 | .025 |
| #18 | A1 | .076 | 0 | .131 | .059 | .075 | 0 | .116 | .029 |
| | A2 | .062 | 0 | .108 | .049 | .069 | 0 | .109 | .025 |
| #19 | A1 | .049 | 0 | .056 | .023 | .044 | .056 | .056 | .097 |
| | A2 | .051 | 0 | .050 | .020 | .034 | .046 | .052 | .091 |
| #20 | A1 | .149 | 0 | .220 | .077 | .237 | .304 | .333 | .294 |
| | A2 | .106 | 0 | .188 | .056 | .227 | .277 | .325 | .273 | whereas the β-casein A2 variant is not. A digestion resistant fragment of these caseins can bind to antigen presenting cells in humans and in the case of diabetics an increased response to the β-casein A1 variant can be observed.

Together with the epidemiological observations on the difference in diabetes incidence in children receiving large amounts of β-casein A1 and A2 variants such as found in the Finish diet compared with those receiving only a β-casein Best discriminant is
  IgG1+3 against A1 beta casein 18/20 v 9/20(p=0.003)
  IgG2+4 13/20 v 9/20(p=0.204)
  The ratio of response of IgG1+3 to the two beta caseins also appears to be different between diabetics and normals with those of the diabetics being higher.
  (9/20 diabetics have a ratio of >1.3 whereas 0/20 have this high a ratio among the normals (p=0.001)

IgG (1+3) represents a Th1 ('helper') response whereas (IgG+4) represents a Th2 ('suppressor') response.

From this data it appears likely that diabetics more often than normals:

1) mount an immune response to beta caseins,
2) that these are more often an IgG1+3 response than a IgG2+4 response, and
3) that these responses are more often directed to A1 beta casein than the A2.

REFERENCES

Aschaffenburg R and Drewry J (1955) *Nature,* 176, 218–219

Ng-Kwai-Hang, K F, Hayes, J F, Moxely, J E and Monardes, H G (1984) *J Dairy Sci,* 67 835–840

Creamer, L K (1991) *Bulletin of the International Dairy Federation* Advanced Dairy Chemistry—Vol 1: Proteins, 261. International Dairy Federation, Brussels, Belgium Grosclaude F (1988) *Productions Animates,* INRA, 1, 5–17

Fox P F and Flynn A (1992) *Advanced Dairy Chemistry—Vol 1: Proteins* (Ed. Fox P F) Elsevier Science Publishers Ltd, London, pp 255–284

Hill J P (1993) *J Dairy Sci,* 76 281–286

Meisel H and Schlimme E (1990) *Trends in Food Science and Technology,* X, 41–43

Mepham T B, Gaye P, Main, P and Mercier J C (1992) *Advanced Dairy Chemistry—Vol 1: Proteins* (Ed. Fox P F) Elsevier Science Publishers Ltd, London, pp 491–543

M'hamiel Jaziri et al (1992) *Biochim, Biophys, Acta,* 1160 251–261

Migliore-Samour D, Floch and Jolles P (1989) *J Dairy Res,* 56, 357–362

Muller L L (1986) *Developments in Dairy Chemistry—1: Proteins* (Ed. Fox P F) Elsevier Science Publishers Ltd, London, pp 315–337

Ng-Kwai-Hang, K F and Grosclaude F (1992) *Advanced Dairy Chemistry—Vol 1: Proteins* (Ed. Fox P F) Elsevier Science Publishers Ltd, London, pp 405–455

Singh H and Creamer L K (1991) *J Dairy Res,* 58, 269

Swaisgood H E (1992) *Advanced Dairy Chemistry—Vol 1: Proteins* (Ed Fox P F) Elsevier Science Publishers Ltd, London, pp 63–110

Sheard N F (1993) *Nutrition Reviews,* 51 79–89

Leslie, R D & Elliott R B (1994): Early Environmental Events As a Cause of IDDM-Evidence & Implications. *Diabetes* 43, 843–850.

Virtanen, S M; Rasanen L; Ylonen K; Aro A; Clayton D; Langholz B; Pitkaniemi J; Savilahti E; Lounamaa R; Tuomilehto J; Akerblom, H K; Childhood Diabetes in Finland (1993) Early Introduction of Dairy Products Associated with Increased Risk of DDM in Finnish Children. The Childhood in Diabetes in Finland Study Group. *Diabetes* 42 (12, Dec), 1786–1790.

Elliott R B & Martin J M (1984): Dietary Protein: A Trigger of insulin-dependent diabetes in the B B Rat? *Diabetologia* 26, 297–299.

Elliott R B (1992): Epidemiology of Diabetes in Polynesia and New Zealand. In: Epidemiology and etiology of Insulin-Dependent Diabetes in the Young. Vol 21. (Eds: Levy-Marchal, C; Czernichow, P), *Pediatr. Adosesc. Endocrinol,* Karger, Basal, 66–71

Elliott R B, Bibby N; Reddy S (1992): "Casein Peptide Precipitates diabetes in the NOD Mouse and Possibly Humans". In Genetic and Environmental Risk Factors for Type 1 Diabetes (IDDM), Including a Discussion on the Autoimmune Basis. Eds: Laron Z and Karp M Freund Publishing House Ltd.

S Lien, P Alestrom, H Klungland and S Rogne (1992) *Animal Genetics* 23, 333–338.

Southward, C R & Walker N L (1980) The Manufacture and Industrial Use of Casein. *New Zealand Journal of Dairy Science and Technology,* 15, 201–217.

Servaas Visser, Charles J Slangen, Fija M Lagerwerf, William D Van Dongen, Johan Haverkamp: Identification of a new genetic variant of bovine β-casein using reversed-phase high-performance liquid chromatography and mass spectrometric analysis, *Journal of Chromatography A,* 711 (1995)141–150.

We claim:

1. A method of producing milk for administration to a diabetes susceptible individual, comprising selecting a lactating bovine cow whose milk contains non-diabetogenic variants of β-casein, which have a proline at amino acid position 67, and does not contain diabetogenic variants of β-casein, which have a histidine at amino acid position 67, milking the so selected bovine cow, and recovering the milk so produced.

2. A method as claimed in claim 1 wherein said cow is selected by testing its milk to determine which non-diabetogenic β-casein variant is present and which diabetogenic β-casein variant is present therein.

3. The method as claimed in claim 2 wherein said method of testing comprises (a) providing a sample of the milk, (b) analyzing the β-casein variants in the milk sample by polyacrylamide gel electrophoresis using an acid urea gel, and (c) determining the presence or absence of the appropriate variants.

4. A method as claimed in claim 2 wherein said method of testing comprises (a) providing a sample of the milk, (b) analyzing the β-casein variants in the milk sample by mass spectrometry, and (c) determining the presence or absence of the appropriate β-casein variants.

5. The method as claimed in claim 4 wherein said mass spectrometry comprises electrospray ionisation mass spectrometry.

6. The method as claimed in claim 4 wherein said mass spectrometry comprises fast atom bombardment mass spectrometry.

7. The method according to claim 5 in which said electrospray ionisation mass spectrometry is followed by fast atom bombardment mass spectrometry.

8. The method as claimed claim 1 wherein said process includes the additional step of processing said milk into milk products.

9. The method as claimed in claim 1 wherein said non-diabetogenic variant is the A2 variant of β-casein.

10. The method as claimed in claim 1 wherein said non-diabetogenic variant is the A3, D or E variant of β-casein.

11. The method as claimed in claim 1 wherein said diabetogenic variant is the A1 variant of β-casein.

12. The method as claimed in claim 1 wherein said diabetogenic variant is the B, C and F variants.

13. The method as claimed in claim 2, further comprising processing said milk into milk products.

14. A method for reducing the risk of contracting type 1 diabetes in a susceptible individual, the method comprising restricting the milk or milk product, other than a casein hydrolysate, intake of that individual to bovine cow milk or a bovine cow milk product which contains non-diabetogenic variants of β-casein, which have a proline at amino acid position 67, and does not contain any diabetogenic variants of β-casein, which have a histidine at amino acid position 67.

15. The method as claimed in claim 14 wherein said non-diabetogenic variant is the A2 variant of β-casein.

16. The method as claimed in claim 14 wherein said non-diabetogenic variant is the A3, D or E variant of β-casein.

17. The method as claimed in claim 14 wherein said diabetogenic variants comprise the A1 variant of β-casein.

18. The method as claimed in claim 14 wherein said diabetogenic variants comprise any one of the B, C and F variants.

19. The method as claimed in claim 14 wherein said susceptible individual is an infant or young child.

20. A method of producing a milk product comprising processing the milk of a bovine cow whose milk does not contain diabetogenic variants of β-casein, which have a histidine at amino acid position 67, into said milk product.

21. The method of claim 20 wherein said milk product is skim milk, and said process comprises the step of separating cream from whole milk.

22. The method of claim 20 wherein said milk product is a milk protein concentrate.

\* \* \* \* \*

UNITED STATES PATENT AND TRADEMARK OFFICE
CERTIFICATE OF CORRECTION

PATENT NO.       : 6,451,368 B1                                            Page 1 of 1
APPLICATION NO.  : 08/836778
DATED            : September 17, 2002
INVENTOR(S)      : Elliott et al.

It is certified that error appears in the above-identified patent and that said Letters Patent is hereby corrected as shown below:

On the title page, (30) Foreign Application Priority Data, delete "April 11, 1994" and insert --November 4, 1994--.

Signed and Sealed this

Twentieth Day of February, 2007

JON W. DUDAS
*Director of the United States Patent and Trademark Office*